United States Patent [19]

Willis

[11] Patent Number: 5,017,912

[45] Date of Patent: May 21, 1991

[54] ELECTRICAL DETECTION OF SHEAR PIN OPERATION

[75] Inventor: John M. Willis, Arlington, Tex.

[73] Assignee: Bell Helicopter Textron Inc., Fort Worth, Tex.

[21] Appl. No.: 422,641

[22] Filed: Oct. 17, 1989

[51] Int. Cl.$^5$ ............................................. G08B 21/00
[52] U.S. Cl. ................................... 340/679; 340/652; 340/682
[58] Field of Search ........................ 340/679, 682, 652

[56] References Cited

U.S. PATENT DOCUMENTS 4,636,778  1/1987  Corkran et al. .................... 340/679
4,714,917  12/1987  Counter et al. .................... 340/679

Primary Examiner—Glen R. Swann, III
Attorney, Agent, or Firm—Richards, Medlock & Andrews

[57] ABSTRACT

A shear detection circuit includes a resistive element in series with another resistor for providing an electrical signal at a node proportional at the value of the resistors when a voltage potential is applied to the detection circuit. The electrical signal is compared to a known value to permit detection of a severed shear pin or an open or short circuit in the detection circuit. The electrical signal is monitored by a computer for displaying the status of the shear pin and the detector circuit and for storing the status of the shear pin and the shear detection circuit for maintenance or repair.

17 Claims, 1 Drawing Sheet

ELECTRICAL DETECTION OF SHEAR PIN OPERATION

This invention was made with government support under contract No. N00019-85-C-0145, awarded by the Department of the Navy, Naval Air Systems command. The government has certain rights in the invention.

BACKGROUND OF THE INVENTION

This invention relates to the detection of a sheared element in a mechanical structure, and, in particular, to a method and apparatus for electrical detection and reporting of a sheared element.

Mechanical equipment utilizes shearing elements or shearing pins to limit the mechanical load so that the shearing element is destroyed to prevent the application of an excessive mechanical load which would damage the equipment. Sheared elements are replaced during the repair of the equipment. Shear pins have been used in aircraft equipment to prevent damage or destruction to the equipment when mechanical loads exceed a predetermined limit.

The detection and reporting of destroyed or sheared shear pins is necessary for their replacement and the continued safe operation of the equipment. A sheared pin in a remote section of a large piece of equipment, such as an aircraft, may not be known or reported unless it is detected and reported through an electrical circuit to a data collection point. Electrical detection means have been used in the past. Such means has a wire that goes through the shear pin and is insulated from it. An excessive mechanical load limit causes the shear pin to shear which hopefully cuts the wire in two, providing an indication that the shear pin had sheared. Shear pins of this type have a disadvantage in that failure of the wire to shear cleanly may prevent the shear pin from acting as a full shear. Such wire type shear pins also have a disadvantage in that the shearing action may cause the wire to short, resulting in a failure to detect and report the sheared pin. Further, in applications where the sheared pin is constantly monitored, an open circuit may occur and the monitoring system is unable to distinguish whether the signal is the result of a sheared pin or whether the wire circuit has opened. In addition, with wire type shear pins an electrical short between the wires outside of the shear pin or an electrical short between the wires and "ground" would preclude detection of the sheared pin. Thus, there is a need for an apparatus and a method for reducing the problems with prior electrical detection of shear pins and to more accurately distinguish between a sheared element and wiring anomalies.

SUMMARY OF THE INVENTION

A shear pin with electrical resistance characteristics is positioned to be sheared or crushed by shearing forces resulting from excess mechanical load. The nature of common graphite resistive materials provides a brittle, clean shearing action, avoiding a possible short circuit from the shearing action of a metallic wire conductor. The resistive type shear pin is connected in series between second and third resistors of known value so when a voltage is applied to the electrical detection circuit, an electrical signal ($e_{s1}$) is provided at a first node between the first and second resistor with a value in proportion to the ratio of the resistors and a second electrical signal ($e_{s2}$) is provided at a second node between the first and third resistors with a value in proportion to these resistors. The electrical detection circuit of the present invention provides signals so a computer can distinguish between electrical wiring anomalies (short or open circuits) and the mechanical shear pin action.

BRIEF DESCRIPTION OF THE DRAWINGS

For a more complete understanding of the present invention and for further advantages thereof, reference is made to the following Description of the Preferred Embodiment taken in conjunction with the accompanying drawings in which.

DETAILED DESCRIPTION

Figure 1:
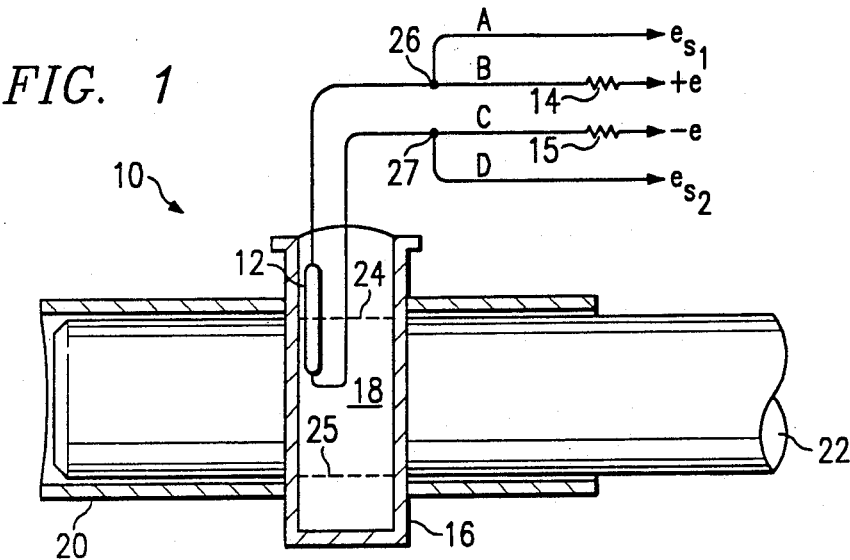
FIG. 1 is an elevational view of a first embodiment of the invention in a hollow type shear pin assembly.

Referring to FIG. 1, a shear detection assembly of the present invention is generally identified by the reference numeral 10. A first resistive element 12 of known resistance is connected in series with a second resistor 14 and third resistor 15 also of known resistance. The first resistor 12 is positioned a predetermine depth within a hollow metal shear pin 16 by a compound 18 which also insulates the resistor 12 from the pin 16. An outer tube 20 has an inner rod 22 slidably engaged within tube 20, and the shear pin 16 is placed through a central opening in said tube 20 and rod 22. The shear pin 16 is designed to shear when a mechanical force transmitted along the rod 22 exceeds the predetermined mechanical load limit.

The first resistor 12 is a carbon-type resistor of a predetermined value and located in a position along a shear line 24 of the shear pin 16. Alternatively, the resistor 12 may be located along the shear line 25. A node 26 is located between the first resistor 12 and second resistor 14. Node 27 is located between the first resistor 12 and a third resistor 15. When known voltages are applied to the series connected resistors, electrical signals ($e_{s1}$ and $e_{s2}$) provide voltages proportional to the value of the resistors 12, 14 and 15.

In operation, the shear pin 16 is engaged within the inner rod 22 and outer tube 20 during normal operation of the equipment. When the mechanical load transmitted through the inner rod 22 and along its central axis exceeds a desired level, the shear pin 16 is designed so that it will shear along lines 24, 25, resulting in the severing or crushing of the first resistor 12 located within the shear pin 16. Upon the severing or crushing of the first resistor 12, the electrical signals $e_{s1}$ and $e_{s2}$ rise to a known value, nominally $+e$ and $-e$, respectively. Resistor 12 may be a commercially available resistor made from a carbon type material, providing a brittle element for more positive shearing action than a metallic wire element. The shear detection assembly 10 of the present invention provides a means of separating circuit anomalies (short and open circuits) from actual shear pin operation as identified in Table I below.

TABLE I

Condition For Detection of Sheared Pin

TABLE I-continued $e_{s1} = +e$
or
$e_{s2} = -e$
Condition for Detection of Open Wire
Open wire A:     $e_{s1} = 0$
Open wire B:     $e_{s1} = -e$
Open wire C:     $e_{s2} = +e$
Open wire D:     $e_{s2} = 0$
Conditions For Detection of Wire Short to Ground
Wire A and/or B:     $e_{s1} = 0$, and $0 > e_{s2} > -e$
Wire C and/or D:     $e_{s2} = *0$, and $0 < e_{s1} < +e$ The first resistor 12 may be a commercially available, carbon-type resistor with its central axis positioned along and substantially perpendicular to one of the shear lines 24, 25. Of course, the first resistor 12 may be positioned elsewhere as long as it is crushed or sheared when the mechanical load limit exceeds the level set for the equipment. As further illustrated in FIG. 4 and described herein below, the signals $e_{s1}$ and $e_{s2}$ may be monitored by a computer system to detect and report the status of the shear detection assembly 10 and any electrical failure in the wiring of the assembly 10 in accordance with the logic of Table I.

Figure 2:
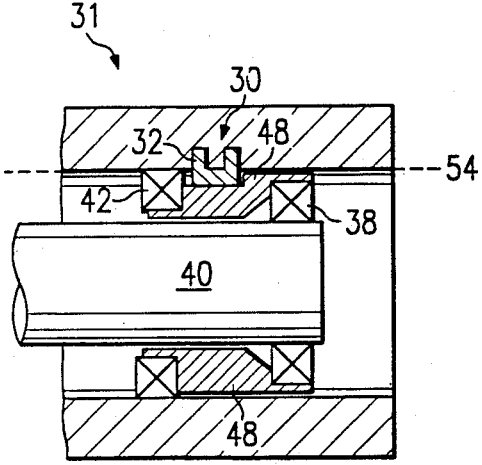
FIG. 2 is an elevational view of a second embodiment of the invention in a redundant bearing mechanism.
Figure 3:
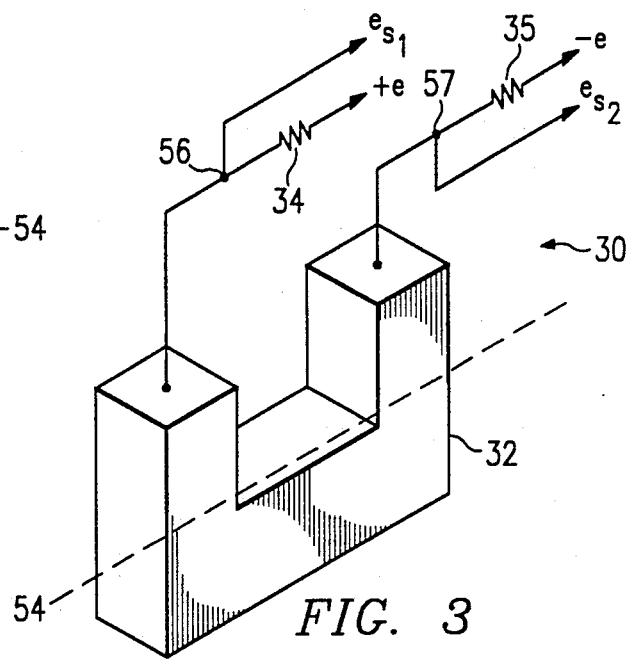
FIG. 3 is an enlarged perspective view of the resistive shear element illustrated in FIG. 2.

Referring to FIGS. 2 and 3, a second embodiment of a shear detection assembly of the present invention is identified by the reference numeral 30. As shown in FIG. 2, pin 32 provides both the mechanical strength and electrical resistance for a redundant bearing mechanism 31. The relatively low shear strength of the resistive shear pin material is particularly suited for this application since the normal bearing friction is very low and the ratio between primary bearing seizure torque and normal running torque can be very large (several hundred to one). Thus, this concept provides a large margin of safety and precludes false shearing actions due to transient loading conditions and other anomalies. The assembly 31 has redundant bearings with a primary bearing 38 supporting the shaft 40 for rotation. In the event the first bearing 38 seizes because of debris or other causes, excess torque is transmitted via spacer ring 48 causing shear pin 32 to shear along shear line 54, and engage the secondary bearing 42.

Electrical characteristics of the shear pin are isolated from the metal components of the assembly with the use of hard insulating material around the shear pin. A first resistor 32 is connected in series between a second resistor 34 and a third resistor 35.

Referring to FIG. 3, a second embodiment of a shear pin detection assembly is shown. The first resistor 32 is preformed of a resistive material as a generally U-shaped device to operate as a shear pin for the shear detection assembly 30. One embodiment of a first resistor 32 used in a redundant bearing mechanism 31 is a U-shaped shear pin of approximately 0.2 inches in height and 0.04 inches in width with a resistance value for approximately 2 ohms.

A node 56 is selected between the first resistor 32 and second resistor 34 and a node 57 is selected between the resistor 32 and 35. Electrical signals $e_{s1}$ and $e_{s2}$ with voltages determined by the proportional value of the resistors 32 to 34 and 32 to 35 when a voltage is applied to the series connected resistors 32, 34 and 35 of the shear detection assembly 30. The signals $e_{s1}$ and $e_{s2}$ of the shear detection assembly 30 enables the detection of the shearing of first resistor 32 or an open or short circuit in the manner described above for shear detection assembly 10.

Electrically, shear detection assembly 30 operates in an identical manner to the first embodiment of assembly 10.

Figure 4:
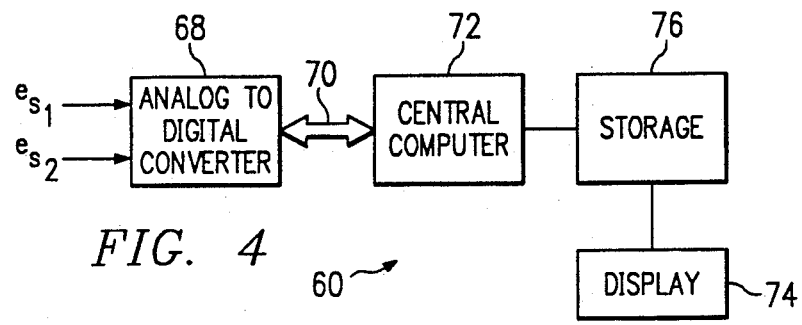
FIG. 4 is a block diagram of the electrical shear detection circuit of the present invention and computer monitoring and reporting system.

Referring to FIG. 4, the shear detection signals $e_{s1}$ and $e_{s2}$ may be applied to a computer monitoring system 60. Signals $e_{s1}$ and $e_{s2}$ are applied to an analog to digital converter 68 and transmitted on a data bus 70 to a central computer 72, which may be part of a system for the equipment using the shear detector assemblies 10 and/or 30. A digitized output of $e_{s1}$ and $e_{s2}$ is monitored through a display 74 for determining the status of the shear detector assemblies 10 and/or 30 of the equipment. In this manner, the operator of the system may determine the status of a number of shear pins at remote locations and to further distinguish a sheared pin signal from an open or short circuit signal in a shear pin electrical detection assembly. The signal monitored by the computer 72 may also be applied to a storage device 76 for later retrieval of the status of the shear pins and the detection circuit for maintenance and repair.

While the present invention has been described with respect to a specific embodiment thereof, various changes and modifications may be suggested to one skilled in the art, and it is intended that the present invention encompass such changes and modifications as fall within the scope of the appended claims.

I claim:

1. An electrical detection circuit for a shearing action, comprising:
    a first resistor positioned perpendicular to a shear line of a device shearing under a mechanical load, said first resistor being destructible when said device shears along said shear line and said first resistor being electrically insulated from said device;
    said first resistor being connected in series between second and third resistors, said second and third resistors being positioned beyond said shear line;
    a first node located between said first and second resistors and a second node located between said first and third resistors, said nodes being positioned beyond said shear line such that a voltage applied to the terminals of said series connected resistors produces an electrical signal $e_{s1}$ at said first node in proportion to the value of said first and second resistors and an electrical signal $e_{s2}$ at said second node in proportion to the value of said first and third resistors, whereby the values of $e_{s1}$ and $e_{s2}$ allow for the detection of the shearing of said first resistor and the presence of wire anomalies in said detector circuit.

2. The electrical detection circuit of claim 1, wherein the said device is a hollow metal shear pin and said first resistor is positioned within said shear pin.

3. The electrical detection circuit of claim 2, wherein said first resistor is said device shearing under a mechanical load.

4. A system for detection of a shearing action in a mechanical structure under a mechanical load along a shear line, comprising:
    a first resistor having a predetermined shear strength positioned on a shear line of the mechanical structure, said first resistor being destructible when the mechanical load exceeds said predetermined shear strength such that said mechanical structure shears along the shear line;
    said first resistor being connected in series between second and third resistors, said second and third resistors being positioned beyond said shear line;

a first node located between said first and second resistors and a second node located between said first and third resistors, said nodes being positioned beyond said shear line such that a voltage applied to the terminals of said series connected resistors produces an electrical signal $e_{s1}$ at said first node in proportion to the value of said first and second resistors and an electrical signal $e_{s2}$ at said second node in proportion to the value of said first and third resistors, whereby the values of $e_{s1}$ and $e_{s2}$ allow for the detection of the shearing of said first resistor and the presence of wire anomalies.

5. A device as in claim 4 further comprising:
a monitoring system positioned and arranged to compare to first value of electrical signal $e_{s1}$ and a second value of electrical signal $e_{s2}$ to predetermined values.

6. A device as in claim 5 wherein said monitor system comprises:
an analog to digital converter for receiving said electrical signals $e_{s1}$ and $e_{s2}$ and having an A-D output;
a computer for monitoring said A-D output, said computer supplying a circuit status signal at a computer output representing the value of signals $e_{s1}$ or $e_{s2}$;
a display connected to said computer output to show said circuit status signal and connected to said computer output; and
storage means for storing said circuit status signal responsive to said computer.

7. A system for detection of a shearing action in a mechanical structure under a mechanical load along a shear line, comprising:
a shear member substantially enclosing a first resistor, said shear member having a predetermined shear strength and being positioned on a shear line of the mechanical structure;
said shear member being destructible when the mechanical load exceeds said predetermined shear strength such that said mechanical structure shears along the shear line;
said first resistor being connected in series between second and third resistors, said second and third resistors being positioned beyond said shear line, and said first resistor being destructible when the mechanical load exceeds said predetermined shear strength;
a first node located between said first and second resistors and a second node located between said first and third resistors, said nodes being positioned beyond said shear line such that a voltage applied to the terminals of said series connected resistors produces an electrical signal $e_{s1}$ at said first node in proportion to the value of said first and second resistors and an electrical signal $e_{s2}$ at said second node in proportion to the value of said first and third resistors, whereby the values of $e_{s1}$ and $e_{s2}$ allow for the detection of the shearing of said first resistor and the presence of wire anomalies.

8. A device as in claim 7 wherein said shear member is substantially electrically isolated from said first resistor.

9. A device as in claim 7 wherein said shear member comprises a hollow metal shear pin and said first resistor is positioned within said hollow metal shear pin.

10. A device as in claim 7 further comprising:
a monitoring system positioned and arranged to compare a first value of electrical signal $e_{s1}$ and a second value of electrical signal $e_{s2}$ to predetermined values.

11. A device as in claim 10 wherein said monitoring system comprises:
an analog to digital converter for receiving said electrical signals $e_{s1}$ and $e_{s2}$ and having an A-D output;
a computer for monitoring said A-D output, said computer supplying a circuit status signal at a computer output representing the value of signals $e_{s1}$ or $e_{s2}$;
a display connected to said computer output to show said circuit status signal and connected to said computer output; and
storage means or storing said circuit status signal responsive to said computer.

12. A method for detection of a shearing action in a mechanical structure under a mechanical load along a shear line with a circuit comprising: a first resistor located on the shear line, a second resistor connected to one end of the first resistor, and a third resistor connected to the other end of the first resistor; comprising the steps of:
monitoring the voltage at the junction between the first and second resistors;
monitoring the voltage at the junction between the first and third resistors;
comparing the monitored voltages with predetermined known voltages; and
generating, in response to said comparing, a signal representing a change in the resistance of the first resistor, said signal having at least two states wherein a first of the two states represents a condition in which the first resistor has broken.

13. A method as in claim 12 further comprising:
producing an electrical signal $e_{s1}$ at a first node in proportion to the value of the first and second resistors;
producing an electrical signal $e_{s2}$ at a second node in proportion to the value of the first and third resistors;
monitoring $e_{s1}$ and $e_{s2}$ to detect the shearing of the first resistor.

14. A method as in claim 12 further comprising:
producing an electrical signal $e_{s1}$ at a first node in proportion to the value of the first and second resistors;
producing an electrical signal $e_{s2}$ at a second node in proportion to the value of the first and third resistors;
monitoring $e_{s1}$ and $e_{s2}$ to detect the presence of wire anomalies.

15. A method as in claim 12 further comprising displaying the status of the first resistor.

16. A method as in claim 12 further comprising displaying of the status of the continuity of the connections between the first, second, and third resistors.

17. A method as in claim 12 further comprising storing a set of data representing the status of the continuity of the connections between the first, second, and third resistors.

* * * * *